US006420551B1

(12) United States Patent
Friesen

(10) Patent No.: US 6,420,551 B1
(45) Date of Patent: *Jul. 16, 2002

(54) ANTISENSE OLIGONUCLEOTIDES TARGETED AGAINST HUMAN IMMUNODEFICIENCY VIRUS

(75) Inventor: Albert D. Friesen, Winnipeg (CA)

(73) Assignee: Viventia Biotech Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/036,637

(22) Filed: Mar. 6, 1998

Related U.S. Application Data

(63) Continuation of application No. 08/782,982, filed on Jan. 14, 1997, now Pat. No. 5,811,537, which is a continuation of application No. 08/308,869, filed on Sep. 19, 1994, now Pat. No. 5,594,122, which is a continuation of application No. 08/081,572, filed on Jun. 23, 1993, now abandoned.

(51) Int. Cl.[7] .......................... C07H 21/04; C12Q 1/68; C12N 15/85
(52) U.S. Cl. ........................ 536/24.5; 435/6; 435/91.1; 435/325; 435/375
(58) Field of Search ........................... 435/6, 440, 91.1, 435/375, 325, 366; 536/23.1, 24.34, 24.5; 514/44

(56) References Cited

U.S. PATENT DOCUMENTS

| | | | |
|---|---|---|---|
| 4,415,732 A | 11/1983 | Caruthers et al. | 536/23.1 |
| 4,458,066 A | 7/1984 | Caruthers et al. | 536/23.1 |
| 4,725,677 A | 2/1988 | Köster et al. | 536/23.1 |
| 4,959,463 A | 9/1990 | Froehler et al. | 536/25.3 |
| 5,110,802 A | 5/1992 | Cantin et al. | 514/44 |
| 5,166,195 A | 11/1992 | Ecker | 514/44 |
| 5,594,122 A | 1/1997 | Friesen | 536/24.5 |

FOREIGN PATENT DOCUMENTS

| | | |
|---|---|---|
| EP | 0375408 | 6/1990 |
| EP | 0386563 | 9/1990 |
| WO | WO 89/08146 | 9/1989 |
| WO | WO 90/06934 | 6/1990 |
| WO | WO 92/02531 | 2/1992 |
| WO | WO 92/10590 | 6/1992 |

OTHER PUBLICATIONS

Branch TIBS 23:45–50, Feb. 1998.*
Matsukura et al. PNAS 86:4244–4248, Jun. 1989.*
Beal et al., "Second structural motif for recognition of DNA by oligonucleotide–directed triple–helix formation" *Science* (1992) 251:1360–1363.
Bennett et al., "Cationic lipids enhance cellular uptake and activity of phosphorothioate entisense oligonucleotides" *Mol. Pharmacol.* (1992) 41:1023–1033.
Capobianco et al., "One pot solution synthesis of cyclic oligodeoxyribonucleotides" *Nucl. Acids Res.* (1990) 18:2661–2669.
Cooney et al., "Site–specific oligonucleotide binding represses transcription of the human c–myc gene in vitro" *Science* (1988) 241:456–459.
Degols et al., "Antisense inhibitors of HIV: problems and perspectives" *Antiviral Res.* (1992) 17:279–287.
*Drug & Market Develop.* "Antisense/oligonucleotide therapeutics: Part 2—Company update" (1993) 4(7/8):179–195.
Fedorova et al., "Complementary addressed modification of double–stranded DNA within a ternary complex" *FEBS Letters* (1988) 228:273–276.
Froehler et al., "Oligodeoxynucleotides containing C–5 propyne analogs of 2'–deoxyuridine and 2'–deoxycytidine" *Tetrahedron Letters* (1992) 33:5307–5310.
Froehler et al., "Triple–helix formation and cooperative binding by oligodeoxynucleotides with a 3'–3' internucleotide junction" *Biochem.* (1992) 31:1603–1609.
Goodchild et al., "Inhibition of human immunodeficiency virus replication by antisense oligodeoxynucleotides" *Proc. Natl. Acad. Sci. USA* (1988) 85:5507–5511.
Horne et al., "Recognition of mixed–sequence duplex DNA by alternate–strand triple–helix formation" *J. Am. Chem. Soc.* (1990) 112:2435–2437.
Iverson et al., "Nonenzymatic sequence–specific cleavage of single–stranded DNA to nucleotide resolution. DNA methyl thioether probes" *J. Am. Chem. Soc.* (1987) 109:1241–1243.
Johnston et al., "Present status and future prospects for HIV therapies" *Science* (1993) 260:1286–1293.
Knorre et al., "Reactive oligonucleotide derivatives and sequence–specific modification of nucleic acids" *Biochimie* (1985) 67:785–789.
Kole et al., "Pre–mRNA splicing as a target for antisense oligonucleotides" *Advanced Drug Delivery Reviews* (1991) 6:271–286.
Lee et al., "Interaction of psoralen–derivatized oligodeoxyribonucleoside methylphosphonates with single–stranded DNA" *Biochem.* (1988) 27:3197–3203.
Lelen, "Ag–biotechnology companies move forward on heels of the FDA statement on biofoods" *Genet. Eng. News* (1992) 12(11):1, 21–22.
Loose–Mitchell, "Antisense nucleic acids as a potential class of pharmaceutical agents" *TIPS* (1988) 9:45–47.
Marcus–Sekura, "Techniques for using antisense oligodeoxyribonucleotides to study gene expression" *Anal. Biochem.* (1988) 172:289–295.
Mathews et al., Analytical strategies for the use of DNA probes *Anal. Biochem.* (1988) 169:1–25.

(List continued on next page.)

*Primary Examiner*—Andrew Wang
(74) *Attorney, Agent, or Firm*—Morrison & Foerster LLP

(57) ABSTRACT

The present invention is directed to oligonuclegtides comprising nucleotide sequences sufficiently complementary to conserved regions of human immunodeficiency virus genetic material such that when bound to said region, the oligonucleotides effectively prevent expression of the genetic material.

6 Claims, 6 Drawing Sheets

OTHER PUBLICATIONS

Matsukura et al., "A new concept in AIDS treatment: An antisense approach and its current status towards clinical application" *Prospects for Antisense Nucleic Acid Therapy of Cancer and AIDS*, Wickström, E., ed., (1991) Wiley–Liss, Inc., New York, pp. 159–178.

Matteucci et al., "Synthesis and crosslinking properties of a deoxyoligonucleotide containing $N^6,N^6$–ethanodeoxyadenosine" *Tetrahedron Letters* (1987) 28:2469–2472.

McGraw et al., "Sequence–dependent oligonucleotide–target duplex stabilities: Rules from empirical studies with a set of twenty–mers" *Biotechniques* (1990) 8:674–678.

Meyer et al., "Efficient, specific cross–linking and cleavage of DNA by stable, synthetic complementary oligodeoxynucleotides" *J. Am. Chem. Soc.* (1989) 111:8517–8519.

Milligan et al., "Current concepts in antisense drug design" *Med. Chem.* (1993) 36:1922–1937.

Praseuth et al., "Sequence–specific binding and photocrosslinking of I and J oligodeoxynucleotides to the major groove of DNA via triple–helix formation" *Proc. Natl. Acad. Sci. USA* (1988) 85:1349–1353.

Ratajczak et al., "In vivo treatment of human leukemia in a scid mouse model with c–myb antisense oligodeoxynucleotides" *Proc. Natl. Acad. Sci. USA* (1992) 89:11823–11827.

Ratner et al., "Complete nucleotide sequence of the AIDS virus, HTLV–III" *Nature* (1985) 313:277–284.

Rittner et al., "Identification and analysis of antisense RNA target regions of the human immunodeficiency virus type 1" *NAR* (1991) 19:1421–1426.

Sanford, "Applying the PCT principle to AIDS" *J. Theor. Biol.* (1988) 130:469–480.

Seela et al., "Oligomers with alternating thymidine and 2'–deoxytubercidin: duplex stabilization by a 7–deazapurine base" *Biochem.* (1985) 24:7556–7561.

Seela et al., "Palindromic octa– and dodecanucleotides containing 2'–deoxyturbercidin: synthesis, hairpin formation, and recognition by the endodeoxyribonuclease EcoRI" *Biochem.* (1987) 26:2232–2238.

Seela et al., "Palindromic oligonucleotides containing 7–deaza–2'deoxyguanosine: solid–phase synthesis of d[(p)GG*AATTCC] octamers and recognition by the endodeoxyribonuclease EcoRI" *Nucl. Acids Res.* (1986) 14:2319–2332.

Shaw et al., "Specific, high–efficiency, triple–helix–mediated cross–linking to duplex DNA" *J. Am. Chem. Soc.* (1991) 113:7765–7766.

Shibahara et al., "Inhibition of human immunodeficiency virus (HIV-1) replication by synthetic oligo–RNA derivatives" *NAR* (1989) 17:239–252.

Stein et al., "Oligonucleotides as inhibitors of gene expression: A review" *Cancer Res.* (1988) 48:2659–2668.

Stein et al., "Antisense oligonucleotides as therapeutic agents—is the bullet really magical?" *Science* (1993) 261:1004–1011.

Sterling, "Systemic antisense treatment reported" *Genet. Eng. News* (1992) 12(12):1, 28.

Thierry et al., "Liposomal delivery as a new approach to transport antisense oligonucleotides" *Gene Regulation: Biology of Antisense RNA and DNA*, Erickson et al., eds., (1992) Raven Press, New York, pp. 147–161.

Uhlmann et al., "Antisense Oligonucleotides: A new therapeutic principle" *Chem. Rev.* (1990) 90:544–584.

van de Sande et al., "Parallel stranded DNA" *Science* (1988) 241:551–557.

Van der Krol et al., "Modulation of eukaryotic gene expression by complementary RNA or DNA sequences" *BioTechniques* (1988) 6:958–976.

Vlassov et al., "Sequence–specific chemical modification of double–stranded DNA with alkylating oligodeoxynucleotide derivatives" *Gene* (1988) 72:313–322.

Wagner, "Gene inhibition using antisense oligodeoxynucleotides" *Nature* (1994) 372:333–335.

Walder, "Antisense DNA and RNA: progress and prospects" *Genes & Devel.* (1988) 2:502–504.

Webb et al., "Hybridization triggered cross–linking of deoxyoligonucleotides" *Nucl. Acids Res.* (1986) 14(19):7661–7674.

Webb et al., "Sequence–specific cross–linking of deoxyoligonucleotides via hybridization–triggered alkylation" *J. Am. Chem. Soc.* (1986) 108:2764–2765.

Weiss, "Upping the antisense ante" *Science News* (1991) 139:108–109.

Whitesell et al., "Stability, clearance, and disposition of intraventricularly administered oligodeoxynucleotides: Implications for the therapeutic application within the central nervous system" *Proc. Natl. Acad. Sci. USA* (1993) 90:4665–4669.

Young et al., "Triple helix formation inhibits transcription elongation in vitro" *Proc. Natl. Acad. Sci. USA* (1991) 88:10023–10026.

Yu et al., *Neurosci Res.* (1991) 30:72–79. Provided as Biosis Acc No. 92138937.

Zon, "Oligonucleotide analogues as potential chemotherapeutic agents" *Pharm. Res.* (1988) 5:539–549.

Zon, "Synthesis of backbone–modified DNA analogues for biological applications" *J. Pro. Chem.* (1987) 6:131–145.

\* cited by examiner

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
ccgcccctcg cctcttgccg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ggctccattt cttgctctcc                                              20

<210> SEQ ID NO 3
<211> LENGTH: 15
<212> TYPE: DNA
<213> ORGANISM: Artificial Sequence
<220> FEATURE:
<223> OTHER INFORMATION: Synthetic Construct

<400> SEQUENCE: 3
ccgcttcttc ctgcc                                                   15

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 1,3,5,7,9,11,14,17,19
<223> OTHER INFORMATION: Base chemically modified by substitution of the
      naturally occurring oxygen of the phosphodiester
      backbone with sulfur to form the corresponding
      phosphorothioate derivatives of the oligomer.

<400> SEQUENCE: 4
ccgcccctcg cctcttgccg                                              20

<210> SEQ ID NO 5
<211> LENGTH: 20
<212> TYPE: DNA
<213> ORGANISM: Artificial Sequence
```

```
<220> FEATURE:
<223> OTHER INFORMATION: Synthetic Construct
<221> NAME/KEY: misc_feature
<222> LOCATION: 1,3,5,7,11,14,17,19
<223> OTHER INFORMATION: Base chemically modified by substitution of the
      naturally occurring oxygen of the phosphodiester
      backbone with sulfur to form the corresponding
      phosphorothioate derivatives of the oligomer.

<400> SEQUENCE: 5
ggctccattt cttgctctcc                                           20

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 1,3,4,10,11,14
<223> OTHER INFORMATION: Base chemically modified by substitution of the
      naturally occurring oxygen of the phosphodiester
      backbone with sulfur to form the corresponding
      phosphorothioate derivatives of the oligomer.

<400> SEQUENCE: 6
ccgcttcttc ctgcc                                                15

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 1,5,10,14,17,19
<223> OTHER INFORMATION: Base chemically modified by substitution of the
      naturally occurring oxygen of the phosphodiester
      backbone with sulfur to form the corresponding
      phosphorothioate derivatives of the oligomer.

<400> SEQUENCE: 7
ggttcttttg gtccttgtct                                           20
```

ANTISENSE OLIGONUCLEOTIDES TARGETED AGAINST HUMAN IMMUNODEFICIENCY VIRUS

This application is a continuation of Ser. No. 08/782,982, filed Jan. 14, 1997, now U.S. Pat. No. 5,811,537, which is a continuation of Ser. No. 08/308,869, filed Sep. 19, 1994, now U.S. Pat. No. 5,594,122, which is a continuation of Ser. No. 08/081,572, filed Jun. 23, 1993, now abandoned.

FIELD OF THE INVENTION

This invention relates to oligonucleotide (ODN) based therapeutics, particularly the treatment of infections of the human immunodeficiency virus (HIV).

BACKGROUND OF THE INVENTION

The present invention relates to ODNs suitable for use in treatment of HIV infected individuals by inhibition of replication of HIV in infected cells.

HIV is responsible for the disease that has come to be known as acquired immune deficiency syndrome (AIDS). Although initially recognized in 1981, no cure has yet been found for this inevitably fatal disease. HIV is spread by a variety of means such as sexual contact, infected blood or blood products and perinatally. Because of the complexity of HIV infection and the paucity of effective therapies, a great deal of effort has been expended in developing methods for detecting, treating and preventing infection. Diagnostic procedures have been developed for identifying infected persons, blood and other biological products.

The HIV genome has been well characterized. Its approximately 10 kb encode sequences containing regulatory segments for HIV replication as well as the gag, pol and env genes coding for the core proteins, the reverse transcriptase-protease-endonuclease, and the internal and external envelope glycoproteins, respectively. HIV tends to mutate at a high rate causing great genetic variation between strains of the viruses and indeed between virus particles of a single infected individual. There are a few "conserved" regions of the HIV genome which tend not to mutate. These regions are presumed to encode portions of proteins essential for virus function which can thus withstand very few mutational events.

The HIV env gene encodes the glycoprotein, gp160, which is normally processed by proteolytic cleavage to form gp120, the external viral glycoprotein, and gp41, the viral transmembrane glycoprotein. The gp120 remains associated with HIV virions by virtue of noncovalent interactions with gp41. These noncovalent interactions are weak, consequently most of the gp1120 is released from cells and virions in a soluble form.

Like most viruses, HIV often elicits the production of neutralizing antibodies. Unlike many other viruses and other infectious agents for which infection leads to protective immunity, however, HIV specific antibodies are insufficient to halt the progression of the disease. Therefore, in the case of HIV, a vaccine that elicits the immunity of natural infection could prove to be ineffective. In fact, vaccines prepared from the HIV protein gp160 appear to provide little immunity to HIV infection although they elicit neutralizing antibodies. The failure to produce an effective anti-HIV vaccine has led to the prediction that an effective vaccine will not be available until the end of the 1990's. Therapeutic agents currently used in treatment of AIDS often cause severe side-effects which preclude their use in many patients. It would, thus, be useful to have alternative methods of treating and preventing the disease that do not entail vaccination and currently available pharmaceutical agents.

Recently, attempts have been made to moderate protein production associated with viral infections by interfering with the mRNA molecules that direct their synthesis. By interfering with the production of proteins, it has been hoped to effect therapeutic results with maximum effect and minimal side effects. It is the general object of such a therapeutic approach to interfere with or otherwise modulate gene expression leading to undesired protein formation.

One method for inhibiting specific gene expression which is believed to have promise is the "antisense" approach. Single-stranded nucleic acid, primarily RNA, is the target molecule for ODNs that are used to inhibit gene expression by an antisense mechanism. A number of workers have reported such attempts: Stein and Cohen (1988) *Cancer Res.*, 48:2659–2668; Walder (1988) *Genes & Development*, 2:502–504; Marcus-Sekura (1988) *Anal. Biochem.*, 172:289–295; Zon (1987) *J. Pro. Chem.*, 6:131–145; Zon (1988) *Pharm. Res.*, 5:539–549; Van der Krol et al. (1988) *Biotechniques*, 6:958–973; and Loose-Mitchell (1988) *TIPS*, 9:45–47. Antisense ODNs are postulated to exert an effect on target gene expression by hybridizing with a complementary RNA sequence. The hybrid RNA-ODN duplex appears to interfere with one or more aspects of RNA metabolism including processing, translation and metabolic turnover. Chemically modified ODNs have been used to enhance nuclease stability and cell permeability.

Duplex DNA can be specifically recognized by oligomers based on a recognizable nucleomonomer sequence. The motif termed "GT" recognition has been described by Beal et al. (1992) *Science*, 25:1360–1363; Cooney et al. (1988) *Science*, 241:456–459; and Hogan et al., EP Publication 375408. In the G-T motif, the ODN is oriented antiparallel to the target purine-rich sequence and A-T pairs are recognized by adenine or thymine residues and G-C pairs by guanine residues.

Sequence-specific targeting of both single-stranded and duplex target sequences has applications in diagnosis, analysis, and therapy. Under some circumstances wherein such binding is to be effected, it is advantageous to stabilize the resulting duplex or triplex over long time periods.

Covalent crosslinking of the oligomer to the target provides one approach to prolong stabilization. Sequence-specific recognition of single-stranded DNA accompanied by covalent crosslinking has been reported by several groups. For example, Vlassov at al. (1986) *Nuc. Acids Res.*, 14:4065–4076, describe covalent bonding of a single-stranded DNA fragment with alkylating derivatives of nucleomonomers complementary to target sequences. A report of similar work by the same group is that by Knorre et al. (1985) *Biochimie*, 67:785–789. It has also been shown that sequence-specific cleavage of single-stranded DNA can be mediated by incorporation of a modified nucleomonomer which is capable of activating cleavage. Iverson and Dervan (1987) *J. Am. Chem. Soc.*, 109:1241–1243. Covalent crosslinking to a target nucleomonomer has also been effected using an alkylating agent complementary to the single-stranded target nucleomonomer sequence. Meyer et al. (1989) *J. Am. Chem. Soc.*, 111:8517–8519. Photoactivated crosslinking to single-stranded ODNs mediated by psoralen has been disclosed. Lee et al. (1988) *Biochem.*, 27:3197–3203. Use of crosslinking in triple-helix forming probes has also been disclosed. Horne et al. (1990) *J. Am. Chem. Soc.*, 112:2435–2437.

Use of $N^4$, $N^4$-ethanocytosine as an alkylating agent to crosslink to single-stranded and double-stranded oligomers has also been described. Webb and Matteucci (1986) *J. Am. Chem. Soc.*, 108:2764–2765; (1986) *Nuc. Acids Res.*, 14:7661–7674; and Shaw et al. (1991) *J. Am. Chem. Soc.*, 113:7765–7766. These papers also describe the synthesis of ODNs containing derivatized cytosine. The synthesis of oligomers containing $N^6$, $N^6$-ethanoadenine and the crosslinking properties of this residue in the context of an ODN binding to a single-stranded DNA has been described. Matteucci and Webb (1987) *Tetrahedron Letters*, 28:2469–2472.

In a recent paper, sequence-specific binding of an octathymidylate conjugated to a photoactivatable crosslinking agent to both single-stranded and double-stranded DNA is described. Praseuth et al. (1988) *Proc. Natl. Acad. Sci. (USA)*, 85:1349–1353. In addition, targeting duplex DNA with an alkylating agent linked through a 5'-phosphate of an ODN has been described. Vlassov et al. (1988) *Gene*313–322; and Fedorova et al. (1988) *FEBS Lett.*, 228:273–276.

In effecting binding to obtain a triplex, to provide for instances wherein purine residues are concentrated on one chain of the target and then on the. opposite chain, oligomers of inverted polarity can be provided. By "inverted polarity" is meant that the oligomer contains tandem sequences which have opposite polarity, i.e., one having polarity 5'→3' followed by another with polarity 3'→5', or vice versa. This implies that these sequences are joined by linkages which can be thought of as effectively a 3'—3' internucleoside junction (however the linkage is accomplished), or effectively a 5'—5' internucleoside junction. Such oligomers have been suggested as by-products of reactions to obtain cyclic ODNs. Capobionco et al. (1990) *Nuc. Acids Res.*, 18:2661–2669. Compositions of "parallel-stranded DNA" designed to form hairpins secured with AT linkages using either a 3'—3' inversion or a 5'—5' inversion have been synthesized. van de Sande et al. (1988) *Science*, 241:551–557. In addition, triple helix formation using oligomers which.contain 3'—3' linkages have been described. Horne and Dervan (1990) *J. Am. Chem. Soc.*, 112:2435–2437; and Froehler et al. (1992) *Biochem.*, 31:1603–1609.

The use of triple helix (or triplex) complexes as a means for inhibition of the expression of target gene expression has been previously adduced (International Application No. PCT/US89/05769). Triple helix structures have been shown to interfere with target gene expression (International Application No. PCT/US91/09321; and Young et al. (1991) *Proc. Natl. Acad. Sci.*, 88:10023–10026), demonstrating the feasibility of this approach.

Various modifications have been found to be suitable for use in ODNs. Oligomers containing 5-propynyl modified pyrimidines have been described. Froehler et al. (1992) *Tetrahedron Letters*, 33:5307–5310. 2'-Deoxy-7-deazaadenosine and 2'-deoxy-7-deazaguanosine have been incorporated into ODNs and assessed for binding to the complementary DNA sequences. Thermal denaturation analysis (Tm) has shown that these substitutions modestly decrease the Tm of the duplex when these analogs are substituted for 2'-deoxyadenosine and 2'-deoxyguanosine. Seela and Kehne (1987) *Biochem.*, 26:2232–2238; and Seela and Driller (1986) *Nuc. Acids Res.*, 14:2319–2332. It has also been shown that ODNs which alternate 2'-deoxy-7-deaza-adenosine and -thymidine can have a slightly enhanced duplex Tm over ODNs containing 2'-deoxyadenosine and -thymidine. Seela and Kehne (1985) *Biochem.*, 24:7556–7561.

2', 3'-dideoxydeazapurine nucleosides have been used as chain terminators for DNA sequencing. 7-propargyl amino linkers are used for incorporation of fluorescent dyes into the nucleoside triphosphates DNA synthesis via amidite and hydrogen phosphonate chemistries has been described. U.S. Pat. Nos. 4,725,677; 4,415,732; 4,458,066; and 4,959,463.

Prior attempts at antisense inhibition of HIV have focused on inhibition of the synthesis of some particular viral protein thought to be essential to the success of the infection and to RNAs which are believed to have important biological function. It has now been found that inhibition of viral gene expression and replication can be more efficiently achieved by targeting the conserved sites of the viral RNAs that signal the synthesis of conserved HIV proteins, particularly the p24 core antigen protein.

SUMMARY OF THE INVENTION

The present invention is directed to ODNs comprising nucleotide sequences sufficiently complementary to conserved regions of human immunodeficiency virus genetic material such that when bound to said region, the ODNs effectively prevent expression of the genetic material.

BRIEF DESCRIPTION OF THE DRAWINGS

FIG. 1 is described in Example 3.

FIG. 2 is described in Example 4.

FIG. 3 is discussed in Example 5.

FIG. 4 is discussed in Example 6.

DETAILED DESCRIPTION OF THE INVENTION

Figure 1:
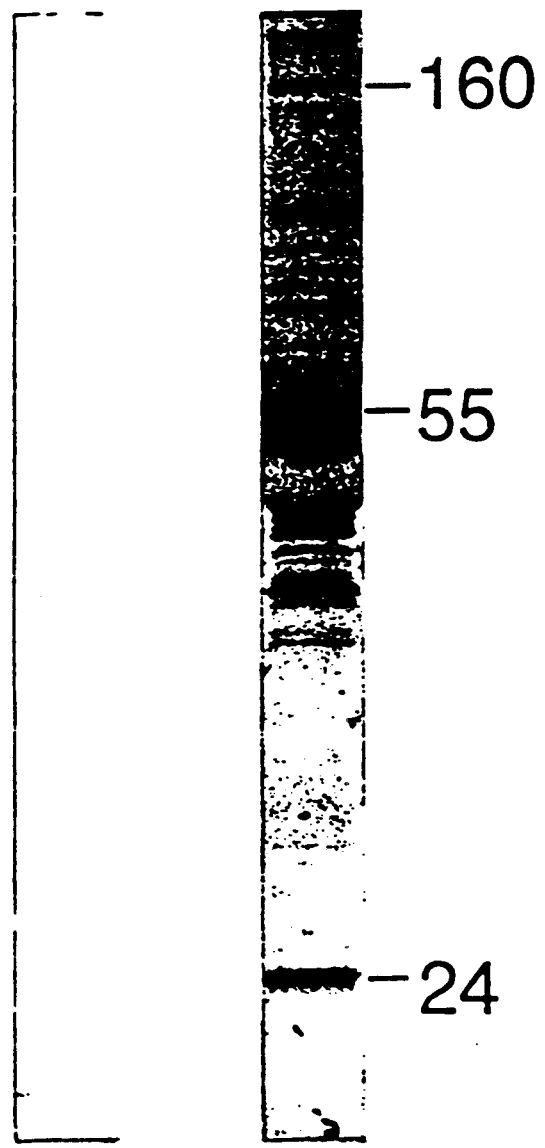
FIG. 1 is an autoradiograph of a SDS-PAGE showing in vivo synthesis of HIV proteins and their breakdown products.

Several conserved sites within HIV RNA have now been found to be effective targets for the inhibition of expression of viral gene products by antisense ODNs and their analogues. The inhibition is based on the capacity to block certain functions during viral replication as measured by production of p24. The clinical importance of p24, a cleavage product of p55, is evidenced by the fact that serum levels of antibody to p24 antigen of HIV provide evidence of the effectiveness of immune response to the virus as well as serving as a marker of free virus in the serum of patients with advanced stage AIDS. Goedert et al. (1989) *N. Engl. J. Med.*, 321:114.

According to the present invention, 20 mer/15 mer sequences were designed and employed as anti-HIV chemotherapeutic agents. The mechanism of action of antisense chemotherapeutics may be solely due to binding to the MRNA or DNA so as to prevent translation or transcription, respectively. The mechanism of action may also be due to activation of RNase H and subsequent degradation of the RNA.

The sequences are conserved in at least two different HIV isolates, and, therefore the antisense ODNs are effective agents against a wide variety of HIV strains.

The sequences were synthesized based on the phosphoramidite chemistry of ODN synthesis on Applied Biosystems model 380D automated DNA synthesizer. They were purified using ODN purification cartridges and/or HPLC.

In therapeutic applications, the ODNs are utilized in a manner appropriate for treatment of a variety of conditions by inhibiting expression of the target genetic regions. For such therapy, the ODNs, alone or in combination can be formulated for a variety of modes of administration, including systemic, topical or localized administration. Techniques and formulations generally can be found in *Remington's Pharmaceutical Sciences*, Mack Publishing Co., Easton, Pa., latest edition. The ODN active ingredient is generally combined with a pharmaceutically acceptable carrier such as a diluent or excipient which can include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the ODNs of the invention are formulated in liquid solutions, preferably in physiologically compatible buffers such as Hank's solution or Ringer's solution. In addition, the ODNs can be formulated in solid form and redissolved or suspended immediately prior to use. Lyophilized forms are also included. Dosages that can be used for systemic administration preferably range from about 0.01 mg/Kg to 50 mg/Kg administered once or twice per day. However, different dosing schedules can be utilized depending on (i) the potency of an individual ODN at inhibiting the activity of its target DNA or RNA, (ii) the severity or extent of the pathological disease state, or (iii) the pharmieokinetic behavior of a given ODN.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, enhancers can be used to facilitate permeation. Transmucosal administration can be through use of nasal sprays, for example, or suppositories. For oral administration, the ODNs are formulated into conventional oral administration forms such as capsules, tablets, and tonics.

For topical administration, the ODNs of the invention are formulated into ointments, salves, gels, or creams, as is generally known in the art. Formulation of the invention oligomers for ocular indications is based on standard compositions known in the art.

In addition to use in therapy, the ODNs of the invention can be used as diagnostic reagents to detect the presence or absence of the target nucleic acid sequences to which they specifically bind. The enhanced binding affinity of the invention ODNs is an advantage for their use as primers and probes. Diagnostic tests can be conducted by hybridization through either double or triple helix formation which is then detected by conventional means. For example, the ODNs can be labeled using radioactive, fluorescent, or chromogenic labels and the presence of label bound to solid support detected. Alternatively, the presence of a double or triple helix can be detected by antibodies which specifically recognize these forms.

The use of ODNs containing the invention substitute linkages as diagnostic agents by triple helix formation is advantageous since triple helices form under mild conditions and the assays can thus be carried out without subjecting test specimens to harsh conditions. Diagnostic assays based on detection of RNA often require isolation of RNA from samples or organisms grown in the laboratory, which is laborious and time consuming, as RNA is extremely sensitive to ubiquitous nucleases.

The ODN probes can also incorporate additional modifications such as modified sugars and/or substitute linkages that render the ODN especially nuclease stable, and would thus be useful for assays conducted in the presence of cell or tissue extracts which normally contain nuclease activity. ODNs containing terminal modifications often retain their capacity to bind to complementary sequences without loss of specificity. Uhlmann et al. (1990) *Chem. Rev.*, 90:543–584. As set forth above, the invention probes can also contain linkers that permit specific binding to alternate DNA strands by incorporating a linker that permits such binding. Froehler et al. (1992) *Biochem.*, 31:1603–1609; and Horne et al. (1990) *J. Am. Chem. Soc.*, 112:2435–2437.

Incorporation of base analogs into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described. Gamper et al. (1986) *Nuc. Acids Res.*, 14:9943.

ODNs of the invention are suitable for use in diagnostic assays that employ methods wherein either the oligomer or nucleic acid to be detected are covalently attached to a solid support as described in U.S. Pat. No. 4,775,619. The ODNs are also suitable for use in diagnostic assays that rely on polymerase chain reaction (PCR) techniques to amplify target sequences according to methods described, for instance, in European Patent Publication No. 0 393 744. ODNs of the invention containing a 3' terminus that can serve as a primer are compatible with polymerases used in PCR methods such as the Taq or Vent™ (New England Biolabs) polymerase. ODNs of the invention can thus be utilized as primers in PCR protocols.

The ODNs are useful as primers that are discrete sequences or as primers with a random sequence. Random sequence primers can be generally about 6, 7, or 8 nucleomonomers in length. Such primers can be used in various nucleic acid amplification protocols (PCR, ligase chain reaction, etc.) or in cloning protocols. The substitute linkages of the invention generally do not interfere with the capacity of the ODN to function as a primer. ODNs of the invention having 2'-modifications at sites other than the 3' terminal residue, other modifications that render the ODN RNase H incompetent or otherwise nuclease stable can be advantageously used as probes or primers for RNA or DNA sequences in cellular extracts or other solutions that contain nucleases. Thus, the ODNs can be used in protocols for amplifying nucleic acid in a sample by mixing the ODN with a sample containing target nucleic acid, followed by hybridization. of the ODN with the target nucleic acid and amplifying the target nucleic acid by PCR, LCR or other suitable methods.

The ODNs derivatized to chelating agents such as EDTA, DTPA or analogs of 1,2-diaminocyclohexane acetic acid can be utilized in various in vitro diagnostic assays as described in, for instance, U.S. Pat. Nos. 4,772,548, 4,707,440 and 4,707,352. Alternatively, ODNs of the invention can be derivatized with crosslinking agents such as 5-(3-iodoacetamidoprop-1-yl)-2'-deoxyuridine or 5-(3-(4-bromobutyramido)prop-1-yl)-2'-deoxyuridine and used in various assay methods or kits as described in, for instance, International Publication No. WO 90/14353.

In addition to the foregoing uses, the ability of the oligomers to inhibit gene expression can be verified in in vitro systems by measuring the levels of expression in subject cells or in recombinant systems, by any suitable method. Graessmann et al. (1991) *Nuc. Acids Res.*, 19:53–59. In the present case, levels of p24 have been measured as indicative of virus replication.

All references cited herein are incorporated herein by reference in their entirety.

The first embodiment of the present invention is an ODN complementary to the region between the 5' long terminal repeat (LTR) and the first initiation codon (AUG) of the a gene. This region contains highly conserved sequences required for efficient viral RNA packaging. Klotman and Wong-Staal (1991) in: The Human Retroviruses by Gallo & Jay, eds. Acad. Press. The antisense ODN is referred to as "anti-gag." The ODN is of sufficient length and complementarity to inhibit expression of the gag gene. The complementary site is from bases +262 to +281 as numbered according to Ratner et al. (1985) *Nature*, 313:277–283. In a preferred embodiment the anti-gag ODN has the specific sequence:

5' CCGCCCCTCGCCTCTTGCCG 3' SEQ ID NO:1

The second embodiment of the present invention is an ODN complementary to the sequence immediately downstream of the major splice acceptor site but upstream of the AUG initiation codon of the tat gene (3' of nucleotide 5358). Translation of this transcript is essential for efficient viral gene expression and replication. The antisense ODN is referred to as "anti-gag-pol." The ODN is of sufficient length and complementarity to inhibit expression of the gag-pol gene. The complementary site is from bases +5399 to +5418 as numbered according to Ratner et al. (1985) *Nature*, 13:277–283. In a preferred embodiment the anti-gag-pol ODN has the sequence:

5' GGCTCCATTTCTTGCTCTCC 3' SEQ ID NO:2

The third embodiment of the present invention is an ODN complementary to the rev gene which is involved in the regulated expression of HIV structural genes. Feinberg et al. (1986) *Cell*, 4:807; and Sodroski et al. (1986) *Nature*, 321:412. It has previously been observed that cytoplasmic RNAs that encode the virion structural proteins gag, pol and env are not found in the absence of a functional rev gene product. Sodroski et al. (1986) Knight at al. (1987) *Science*, 236:837–840; Malim et al. (1988) *Nature*, 335:181–183; and Hadzopoulou-Cladaras et al. (1989) *J. Virol.*, 63:1265–1274. rev mutants of HIV-1 are incapable of inducing the synthesis of the viral structural proteins and are therefore replication defective. Sadaie et al. (1988) *Science*, 239:910. rev is, therefore, said to be important in governing the transition from the expression of the early regulatory genes to that of the late structural genes. Greene (1991) in Mechanisms of Disease. Ed. by F. Epstein. The antisense ODN is referred to as "anti-rev." The ODN is of sufficient length and complementarity to inhibit expression of the rev gene. The complementary site is from bases +5552 to +5566 as numbered according to Ratner et al. (1985) In a preferred embodiment the anti-rev ODN has the following sequence:

5' CCGCTTCTTCCTGCC 3' SEQ ID NO:3

The fourth embodiment of the present invention is an ODN complementary to the region within the second splice acceptor site. This region contains highly conserved sequences required for efficient viral RNA packaging. Klotman and Wong-Staal (1991) in: The Human Retroviruses by Gallo & Jay, eds. Acad. Press. The antisense ODN is referred to as "GPI-2A." The ODN is of sufficient length and complementarity to inhibit expression of the gag gene. The complementary site is from bases +1189 to +1208 as numbered according to Ratner et al. (1985). In a preferred embodiment the anti-gag ODN has the specific sequence:

5' CCGCCCCTCGCCTCTTGCCG 3' SEQ ID NO:1

In a further preferred embodiment, the ODNS were chemically modified by substitution of the naturally occurring oxygen of the phosphodiester backbone with sulfur to form the corresponding phosphorothioate derivatives of the oligomers. The positions of the sulfur are as shown below.

Anti-gag:

5' $C^SCG^SCC^SCC^STC^SGC^SCTC^STTG^SCC^SG$ 3' SEQ ID NO:4;

Anti-gagpol:

5' $G^SGC^STC^SCA^STTTC^STTG^SCTC^STC^SC$ 3' SEQ ID NO:5;

Anti-rev:

5' $C^SCG^SC^STTCTTC^SC^STGC^SC$ 3'SEQ ID NO:6; and

GPI-2A:

5' $G^SGTTC^STTTTG^SGTCC^STTG^STC^ST$ 3' SEQ ID NO:7.

In accordance with the present invention, methods of modulating the expression of the p24 protein are provided. The targeted RNA, or cells containing it, are treated with the ODN analogs which bind to specific regions of the RNA coding for the HIV p24 core structural protein. The RNA targeted sites include regions involved in the mechanism of expression of the HIV p24 core structural protein.

The following examples are intended to illustrate, but not to limit, the invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLE 1

Cell Culture

To determine the effect of antisense oligomer on viral gene expression, B4.14 cells, provided by Dr. David Rekosh, Microbiology Department, University of Virginia, were seeded at a cell density of 5,000–12,000 cells per well in 24-well/35 mm plastic tissue culture plates and were maintained in Iscove's Modified Dulbecco's Medium with 10% calf serum, 50 µg/ml gentamycin and 200 µg/ml hygromycin B at 37° C. in a humidified incubator with 5% $CO_2$ for a few hours. Subsequently, the incubated cells were washed and incubated under the same conditions with medium containing the indicated concentrations of ODN and 10% serum heat inactivated to reduce serum nuclease activity. The same ODN sequences, but with switched polarity were used as controls.

EXAMPLE 2

Viral Antigen Assay

Cells cultured as described in Example 1 were labeled with 75 to 150 $\mu$Ci/ml [$^{35}$S]-methionine (70% L-Methionine/15% L-Cysteine) in the presence of methionine-free medium containing 29.2 mg/100 ml glutamine, 50 $\mu$g/ml gentamycin, 200 $\mu$g/ml hygromycin B. 10% heat inactivated fetal calf serum plus the desired concentration of oligomer. The [$^{35}$S]-methionine concentration was 185 MBq and the specific activity was 1057 Ci/mmole). Labeled samples were subsequently washed with phosphate buffered saline (PBS) and resuspended in 200 $\mu$l lysis buffer comprised of 50 mM Tris, pH 7.2; 150 mM NaCl; 5 mM EDTA; 1% Triton-100; 0.2% Deoxycholic acid.

Culture medium containing labeled virus was treated with 10% Triton X-100 to a 1% final concentration to disrupt virus particles. The samples were preabsorbed with protein A-Sepharose beads for 30 min. at 4° C. [$^{35}$S]-methionine-labeled viral proteins were then immunoprecipitated for 2 hours using protein A-Sepharose beads and 2.5 $\mu$l/sample of polyclonal rabbit antiserum directed against HIV-1 p25/24, obtained from the National Institute of Allergy and Infectious Diseases (AIDS Research and Reference Reagent Program). The antibodies were obtained from National Institute of Allergy & Infectious Disease (AIDS Research & Reference Reagent Program) and MicroGeneSys, Inc.

The resulting pellets were washed 4 times with lysis buffer, once with lysis buffer containing 500 mM NaCl and finally once with TNE buffer comprised of 10 mM Tris, pH 7.2; 25 mM NaCl; 1 mM EDTA. Samples were then resuspended in 20–30 $\mu$l 2X SDS sample buffer, boiled for 5–10 min, applied to a 12.5% SDS polyacrylamide gel electrophoresis and then analyzed by electrophoresis, according to the method described by Laemmli (1970) Nature, 227:680–685. The results obtained are listed in Table 1 and in FIGS. 1–3. Percent inhibition is determined by densitometric analysis of the autoradiography. The first two ODNs (anti-gag and anti-tat) were phosphorothioate derivatives [sulfurization on alternate bases]. Inhibition was observed at ODN concentrations of 5 $\mu$M assayed after 3 days incubation with the oligomer. The third oligomer was a 15-mer phosphodiester derivative. Observed inhibition was at oligomer concentration of 200 $\mu$g/ml assayed after 6 days incubation with the oligomer.

TABLE 1

Preliminary Observation
Inhibition of viral protein synthesis by antisense oligomer in B4.14 cells

| Sequence 5'–3' | Complementary Site | Function | % inhibition |
| --- | --- | --- | --- |
| CCGCCCCTCGCCTCTTGCCG | 262–281 | Splice Donor | 30 |
| GGCTCCATTTCTTGCTCTCC | 5399–5418 | tat initiator | 30 |
| CCGCTTCTTCCTGCC | 5552–5566 | Rev | 40 |

EXAMPLE 3

FIG. 1 is an autoradiograph of a SDS-PAGE showing in vivo synthesis of HIV-1 viral proteins and their breakdown products. The following samples were run. Two hundred 1$\mu$of CMT3 [wild-type (left)] and B4.14 [transfected line (right)] cell lysates following metabolic labeling with [$^{35}$S]-methionine were immunoprecipitated with rabbit serum against p24 viral antigen as described above. The positions of the viral proteins (p160; p55 and p24) are clearly visible in the B4.14 cell lysate but not in control cell line CMT3 cell lysate.

EXAMPLE 4

Figure 2:
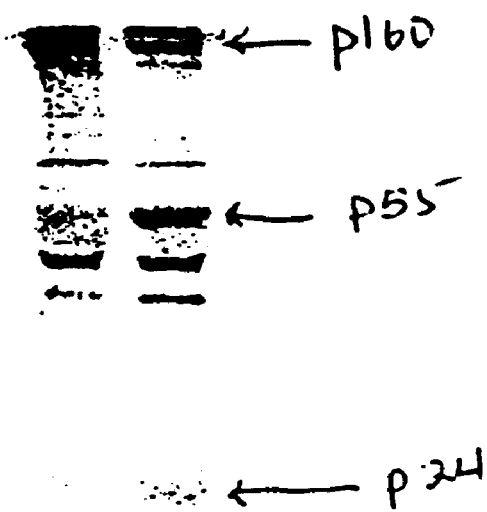
FIG. 2 is an autoradiograph of a SDS-PAGE showing significant inhibition of expression of the HIV proteins by an antisense ODN directed against the rev sequence.

FIG. 2 is an autoradiograph of a SDS-PAGE showing a significant inhibition of expression of HIV proteins by the antisense ODN directed to the rev sequence. The following experiment was performed. Two hundred $\mu$l of B4.14 [transfected line] cell lysates following 3 days treatment with antisense [AS]; and sense, the inverse complement of the antisense oligomer [CS]; and subsequent [$^{33}$S]-methionine labeling were immunoprecipitated with rabbit serum directed against p24 viral antigen as described above. Equal amounts of protein were loaded on each lane.

EXAMPLE 5

Figure 3:
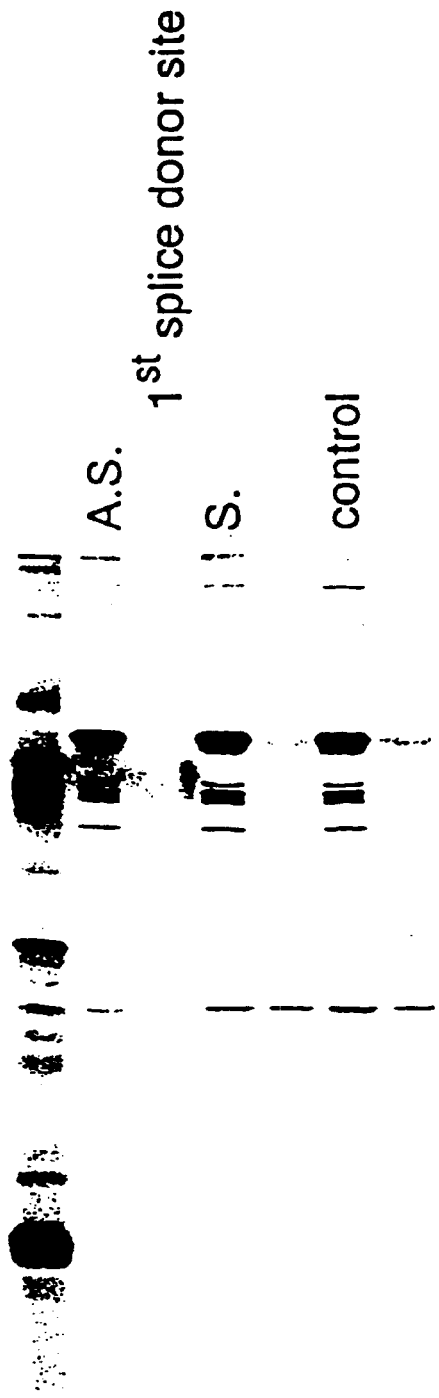
FIG. 3 is an autoradiograph of a SDS-PAGE showing significant inhibition of expression of HIV proteins by antisense ODN directed against the first splice donor site of the HIV-1 genome.

FIG. 3 is an autoradiograph of a SDS-PAGE showing a significant inhibition of expression of HIV proteins by the antisense ODN directed to the first splice site donor of the HIV-1 genome. The following experiment was performed. Two hundred $\mu$l of B4.14 [transfected cell line] cell lysates/medium following 6 days treatment with antisense [AS]; sense, the inverse complement of the antisense ODN [S]; and control [B4.14] cell lysate only); and subsequent $^{35}$S-methionine labeling were immunoprecipitated with rabbit serum directed against p24 viral antigen as described above. Equal amounts of protein were added in each lane.

EXAMPLE 6

The Effects of Different

Concentrations of the Antisense ODNs

To determine whether there was a dose relationship of the antisense ODNs on HIV gene expression, the following experiment was performed.

The cells were cultured as described in Example 1 and incubated overnight with different concentrations of ODNs directed against the first splice donor site in the presence of 5 $\mu$g/ml Lipofectin and 1% heat-inactivated fetal calf serum. The medium was subsequently replaced with fresh medium containing 10% heat-inactivated serum. ODN was then added and incubated for 7 days. Western blot analysis was performed with rabbit polyclonal antibody directed against HIV p24/55 proteins.

Following SDS-polyacrylamide electrophoresis, cellular proteins were electrophoretically transferred to Immobilon membrane (Schleicher and Schuell) as follows. An Immobilon membrane was placed in methanol in a clean dish, washed several times in deionized distilled water and soaked in western transfer buffer (60.6 g Tris-HCl; 288 g glycine; 4 l methanol and distilled water to 20 l ). The apparatus used is the Dio-Rad Trans-Blot cell, used according to the manufacturer's instructions. Western blot analysis was performed using the Vectastain ABC kit (Alkaline Phosphatase Rapid IgG) (Vector Laboratories) according to the manufacturer's instructions.

Figure 4:
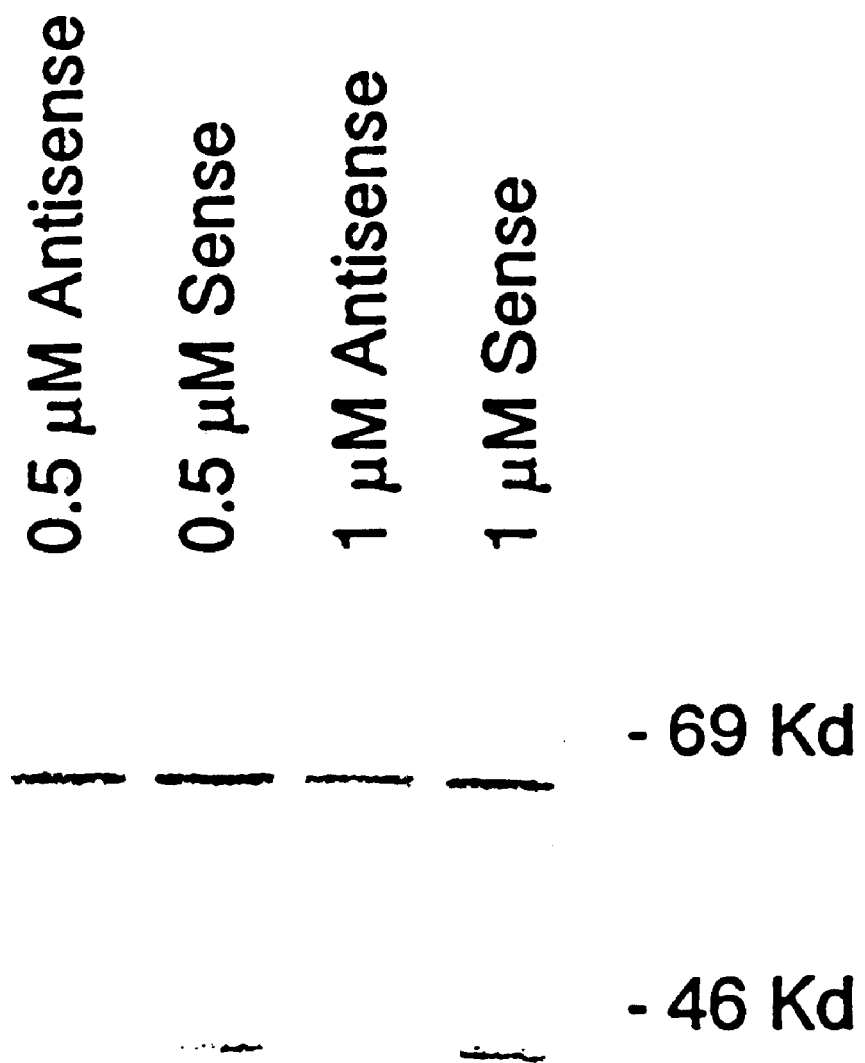
FIG. 4 is an autoradiograph of a SDS-PAGE showing the effects of different concentrations of antisense ODNS on HIV-gene product synthesis.

The results are shown in FIG. 4 where it can be seen that 0.5 and 1 $\mu$M antisense ODN are equally effective at preventing p24 synthesis.

EXAMPLE 7

The Effects of Different Concentrations of the ODN GPI-2A

To determine the ability of the ODN GPI-1A to inhibit expression of p24 in HIV infected cells, the following experiments were performed.

Figure 5:
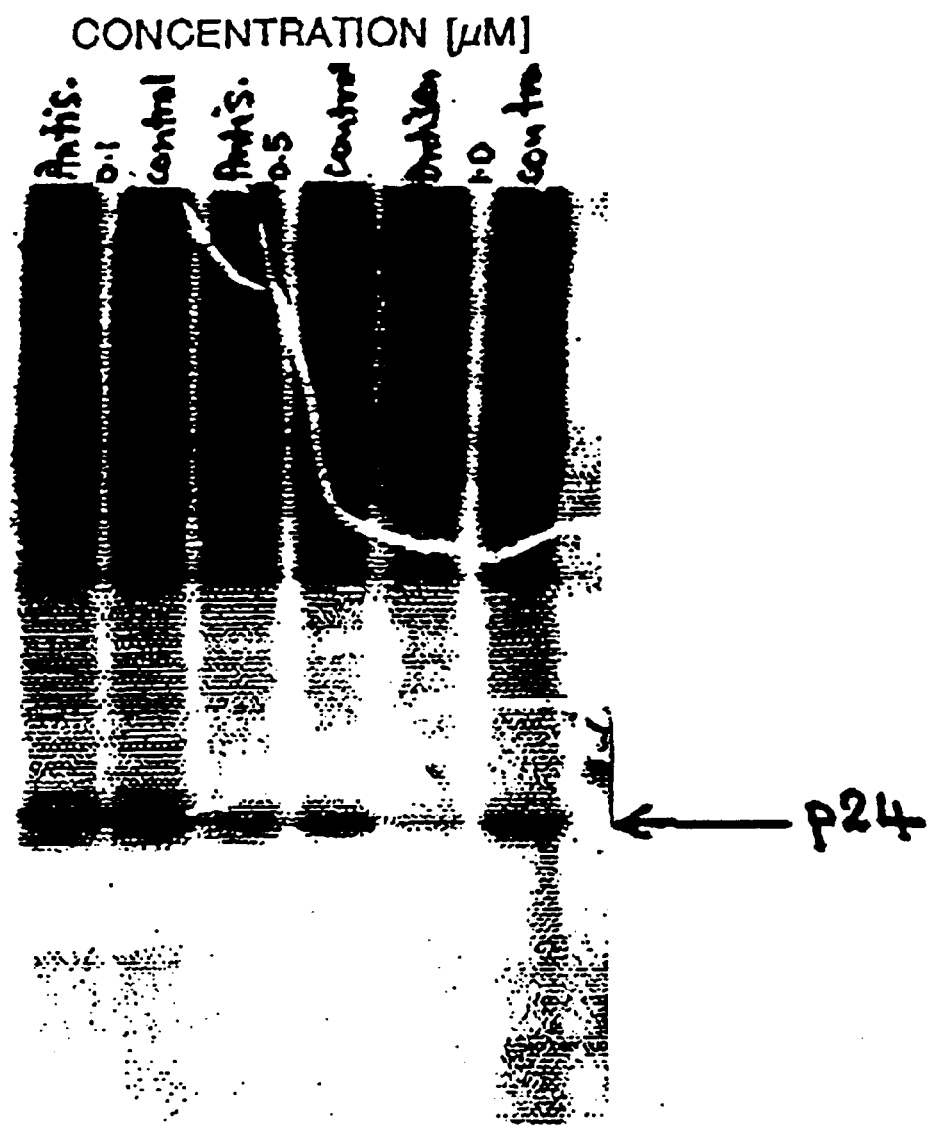
FIG. 5 is an autoradiograph of a SDS-PAGE showing the concentration dependent inhibitory effects of ODN GPI-2A on p24 expression in HIV infected cells.

Cells were incubated overnight with 0.1, 0.5 and 1.0 µM of the ODN in the presence of 1% heat-inactivated fetal calf serum. The serum concentration was subsequently raised to 10% and incubated for 3 days. About $3\times10^7$ cpm/probe was immunoprecipitated using rabbit polyclonal antibody directed against p24/25 viral proteins as described above. The lane marked control had the sense strand, the inverse complement of the antisense oligomer, added to the cells rather than the sense strand. The autoradiograph in FIG. 5 shows that there was a dose-dependent inhibition of the HIV viral core antigen, among others.

Figure 6:
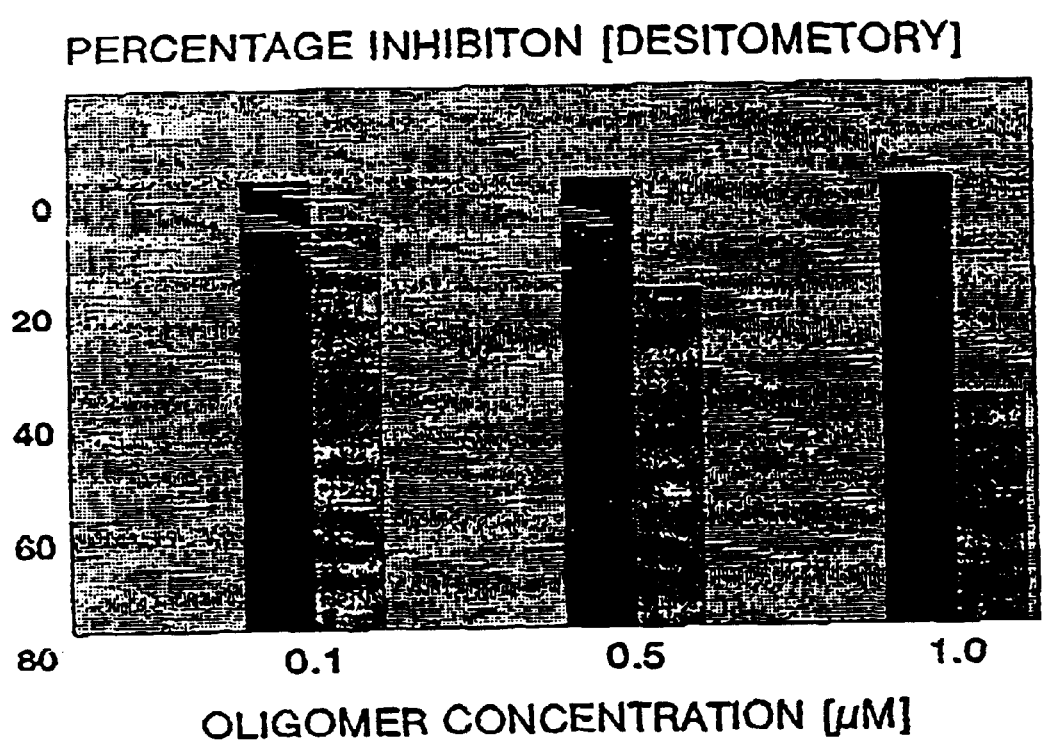
FIG. 6 is a bar graph showing the concentration dependent inhibitory effects of ODN GPI-2A on p24 expression in HIV infected cells.

The autoradiograph was then subjected to densitometry analysis. The results, presented in FIG. 6, indicate that at 1.0 µM, the ODN inhibited about 50% of the p24 synthesis.

What is claimed is:

1. At least one oligonucleotide comprising a nucleotide sequence sufficiently complementary to a region of human immno-deficiency virus genetic material such that when bound to said region, the oligonuclcotide inhibits expression of the genetic material wherein the nucleotide sequence is complementary to the nucleic acid sequences selected from the group consisting of: +5399 to +5418, and +5552 to +5566.

2. The at least one oligonucleotide according to claim 1 wherein the nucleotide sequence is selected from the group consisting of:

5' GGCTCCATTTCTTGCTCTCC 3' (SEQ ID NO:2); and

5' CCGCTTCTTCCTGCC 3' (SEQ ID NO:3).

3. The at least one oligonucleotide according to claim 1 wherein the nucleotide sequence is selected from the group consisting of;

$5^S$ $G^S GC^S TC^S CA^S TTTC^S CTC^S TC^S C$ 3' (SEQ ID NO:5); and $5^S C^S CG^S C^S TTCTTC^S C^S TGC^S C$ 3' (SEQ ID NO:6) wherein S stands for a sulfur atom.

4. A composition comprising an oligonucleotide and according to claim 1 or 2 a pharmaceutically acceptable carrier therefor.

5. The composition according to claim 4, further comprising a liposome preparation.

6. The composition according to claim 5, wherein the liposome preparation comprises lipofectin.

* * * * *